United States Patent
Okumura et al.

(10) Patent No.: US 6,187,336 B1
(45) Date of Patent: Feb. 13, 2001

(54) PROCESS FOR PRODUCING A SOLID WHICH IS RAPIDLY SOLUBLE IN THE ORAL CAVITY

(75) Inventors: Mutsuo Okumura; Sachio Motegi; Tadashi Ukigaya; Katsuaki Miyazaki, all of Saitama (JP)

(73) Assignee: Nikken Chemicals Co., Ltd., Tokyo (JP)

( * ) Notice: Under 35 U.S.C. 154(b), the term of this patent shall be extended for 0 days.

(21) Appl. No.: 09/172,018

(22) Filed: Oct. 14, 1998

(30) Foreign Application Priority Data

Nov. 14, 1997 (JP) .................................................. 9-329743

(51) Int. Cl.[7] .............................. A61K 9/20; A61K 9/14; A61K 9/50
(52) U.S. Cl. ......................... 424/464; 424/465; 424/488; 424/499
(58) Field of Search .................................... 424/464, 451, 424/489

(56) References Cited

U.S. PATENT DOCUMENTS

| 5,501,861 | * | 3/1996 | Makino et al. | 424/464 |
| 5,525,354 | * | 6/1996 | Posti et al. | 424/451 |
| 5,720,974 | * | 2/1998 | Makino et al. | 424/464 |
| 5,945,127 | * | 8/1999 | Breitenbachet et al. | 424/489 |

* cited by examiner

*Primary Examiner*—Thurman K. Page
*Assistant Examiner*—Isis Ghali
(74) *Attorney, Agent, or Firm*—Sughrue, Mion, Zinn, Macpeak & Seas, PLLC

(57) ABSTRACT

A rapidly soluble solid in the oral cavity comprising erythritol, which has a porous structure; and a process for producing a rapidly soluble solid in the oral cavity comprising erythritol, which comprises the steps of: preparing a composition comprising erythritol and appropriate moisture, kneading the composition, molding the kneaded composition, and drying the molded composition under reduced pressure.

25 Claims, No Drawings

PROCESS FOR PRODUCING A SOLID WHICH IS RAPIDLY SOLUBLE IN THE ORAL CAVITY

BACKGROUND OF THE INVENTION

1. Field of the Invention

The present invention relates to a rapidly soluble solid in the oral cavity, particularly, a rapidly soluble preparation in the oral cavity. Also, the present invention relates to a process for producing the same.

2. Background Art

Recently, a novel dose form has been sought for patients having difficulty in swallowing, such as the aged, infants and the like. For example, disintegrating preparations in the oral cavity, jellies, and pastes have been suggested. Particularly, disintegrating preparations in the oral cavity, which can easily be taken without water in any place at any time, would be suitable for the aged, infants and the like.

Generally, disintegration properties and hardness of tablets conflicts with each other. To increase the rate of disintegration for improving disintegration properties leads to decreased tablet hardness. However, it is important for tablets to have a certain degree of hardness while the tablets are transported and packaged in factories or distributed through the market or when a patient takes the tablet out of the package. A tablet having insufficient hardness fails to retain its shape and can crumble in these situations.

Under these circumstances, various techniques for producing rapidly soluble preparations in the oral cavity have been proposed.

For example, JP-B-58-24419 (the term "JP-B" as used herein means an "examined Japanese patent publication") discloses a process for producing easily disintegrating porous tablets which comprises mixing a pharmaceutical composition with a solvent capable of freezing and inert to the composition, solidifying the solvent in an inert cooling medium, compressing the mixture into tablets at a temperature lower than the freezing point of the solvent, and evaporating the solvent by freeze-drying or spontaneous drying.

Commercially available rapidly soluble preparations in the oral cavity include Zydis (commercial name) produced by R. P Scherer (England), which is produced by dissolving an active ingredient, a polymer, a saccharide, and the like, followed by freeze-drying.

Additionally, JP-A-5-271054 (the term "JP-A" as used herein means an "unexamined published Japanese patent application") discloses a tablet soluble in the oral cavity and its preparation; JP-A-8-291051 discloses a method for producing rapidly soluble tablet and a rapidly soluble tablet produced by the method; JP-A-8-333243 discloses a tablet having excellent touch in the oral cavity; and JP-A-9-48726 discloses a rapidly disintegrating preparation in the oral cavity and its production.

The techniques disclosed in the above references have their several disadvantages such that the rate of disintegration is insufficient; the tablets, while capable of disintegrating rapidly, fail to have sufficient mechanical strength; or the finished tablets are difficult to handle ordinarily due to high hygroscopicity.

In molding a pharmaceutical composition into solid preparations, such as tablets and the like, a rotary tablet machine is used usually. When a pharmaceutical composition in semi-solid or wet conditions is molded into tablets by using this type of tablet machine, such problems often occur as poor fluidity of the composition to be supplied and adhesion of the composition to a pressing member.

Water-soluble binders (e.g., polyvinylpyrrolidone, hydroxypropyl cellulose, hydroxypropylmethyl cellulose, polyvinyl alcohol, methyl cellulose, gelatin, and the like) are used to increase hardness of tablets. Disintegrants, such as hydroxypropyl cellulose having a low degree of substitution, corn starch, alginic acid, and the like, are used to increase the rate of disintegration. When used in increased amounts; however, the water-soluble binders or disintegrants become sticky as the tablet crumbles in the oral cavity or make the tablet unpleasant to palate.

SUMMARY OF THE INVENTION

To solve the above-described problems of the conventional techniques, the inventors of the present invention have conducted extensive investigations and found, as a result, that preparations obtained by kneading a mixture of erythritol and a drug or the like, together with an appropriate amount of water, molding the mixture into a tablet-like form by means of a single-shot tablet machine, a molding machine or an extrusion molding machine (e.g., extruder), followed by drying in a vacuum drier have sufficient hardness for handling and yet are capable of melting or disintegrating in the oral cavity in an extremely short time (about 10 seconds).

The present invention provides a rapidly soluble solid in the oral cavity comprising erythritol, which has a porous structure or a structure of a porous inside and a dense and hard surface (the solid preferably having a surface hardness of about 3 kg or higher) and is capable of melting or disintegrating in the oral cavity in a short time.

The present invention also provides a process for producing the above-described rapidly soluble solid in the oral cavity comprising erythritol, which comprises the steps of:

preparing a composition comprising erythritol and appropriate moisture, kneading the composition, molding the kneaded composition, and drying the molded composition under reduced pressure.

DETAILED DESCRIPTION OF THE INVENTION

In the present invention, the term "rapidly soluble solid in the oral cavity" means that the time for the solid in the oral cavity of healthy men to completely dissolve or crumble with saliva is about 20 seconds or less, preferable 10 seconds or less, or that the disintegration time of the solid measured with a disintegration tester specified in The Pharmacopoeia of Japan (testing liquid: water at 37° C.) is about 30 seconds or less, preferably 10 seconds or less.

The rapidly soluble solid in the oral cavity according to the present invention is usually intended to be a rapidly soluble preparation in the oral cavity comprising erythritol and a drug, preferably a rapidly soluble tablet in the oral cavity. In addition to the medical use, the rapidly soluble solid in the oral cavity can be made use of as a food. For example, the rapidly soluble solid in the oral cavity can be solid sweeteners, tablet candies, and the like in which erythritol is combined with other sweeteners, flavors, coloring agents, vitamins, acidulants, and the like.

The drug which can be used in the rapidly soluble solid in the oral cavity preparations is not particularly limited so long as it is not affected by erythritol and can be administered orally. Examples of the drugs that especially enjoy the effects of the present invention are drugs for senile dementia, antipyretic, analgesic and anti-inflammatory agents, antitussives, vitamins, psychotropic agents, antivertigo products, hypnotic sedatives, gastrointestinal drugs, antiarrhythmics, hypotensives, and the like.

If the drug is extremely bitter or stinging, it is preferred to mask the particles of the drug with an insoluble or enteric polymer.

The pharmaceutical composition comprising the active ingredient and erythritol can further contain pharmaceutically acceptable additives commonly used in the art, such as sucrose, lactose, xylitol, D-mannitol, maltitol, lactitol, starch, hydroxypropyl cellulose having a low degree of substitution, magnesium stearate, calcium stearate, talc, light silicic acid anhydride, silicon dioxide hydrate, various surfactants, flavors, coloring agents, sweeteners, acidulants, and the like.

The pharmaceutically acceptable additives can be used either individually or as a mixture thereof in arbitrary amounts so long as the disintegrating properties and molding properties are not impaired.

Where the rapidly soluble solid in the oral cavity according to the present invention is a food, such as solid sweeteners, tablet-like candies, and the like, the composition comprises erythritol as a main component and, if desired, other foods or food additives. Examples of useful foods or food additives include high sweetness sweeteners (for example, aspartame, Stevia sweeteners (e.g., stevioside, rebaudioside, enzyme-treated stevia), saccharin sodium, Acesulfame K, and the like); sugar alcohols (for example, sorbitol, maltitol, xylitol, lactitol, isomalt, reducing starch saccharification products, and the like); saccharides (for example, sucrose, glucose, fructose, maltose, isomerized sugar, fructo-oligosaccharide, isomalto-oligosaccharide, and the like); flavors (for example, lemon flavor, orange flavor, cinnamon flavor, rosemary flavor, menthol flavor, and the like); coloring agents (for example, food yellow No. 5, food red No. 2, and the like); vitamins (for example, vitamins A, $B_1$, $B_2$, $B_6$, $B_{12}$, C, E, and the like); acidulants (for example, malic acid, citric acid, tartaric acid, and the like); fruit juices (for example, grape juice, citrus juices, and the like); cacao powder, coffee powder, calcium powder, and the like.

The proportions of additives, such as drug, pharmaceutical additives, food additives, and the like, in the rapidly soluble solid in the oral cavity containing erythritol are not particularly limited, but are preferably 0 to 60% by weight, more preferably 0.1 to 20% by weight, per the solid content of the composition. The rapidly soluble solid in the oral cavity may comprises erythritol alone with no additives, which can be used as a rapidly soluble tablet candy or solid sweetener.

On the other hand, the proportion of the erythritol in the rapidly soluble solid in the oral cavity is not particularly limited, but is preferably 40 to 100% by weight, more preferably 80 to 99.9% by weight, per the solid content of the composition.

The rapidly soluble solid in the oral cavity of the present invention can be prepared as follows. Erythritol and other components such as drugs, pharmaceutical additives, and food additives are usually used as fine particles preferably with an average particle size of 200 μm or less, particularly 100 μm or less. The solid such as a tablet prepared from such finely particulate materials feels satisfactory in the oral cavity with no rough feel while disintegrating.

In the present invention, the term "the appropriate moisture" means that the composition comprises erythritol is prepared so as to have an appropriate moisture content of 5 to 40% by weight, preferably 5 to 20% by weight, more preferably 7 to 20% by weight, per the solid content of the composition. Such a moisture content is usually achieved by addition of water.

A mixed solution of water and an alcoholic organic solvent, such as ethanol, methanol or the like, may be used in place of water to give the abovedescribed moisture. If the mixed solution has too high an organic solvent content, the surface of the molded solid will dry before drying under reduced pressure, failing to secure moderate hardness. A preferred content of the organic solvent, e.g., ethanol, in the mixed solution is about 20% by weight or less when the composition is kneaded, for example, by means of an ordinary kneading machine (e.g., the universal mixing machine used in Examples hereinafter described).

In the present invention, the term "kneading" means a step of thoroughly kneading a composition comprising erythritol and other components (e.g., drug) in the presence of appropriate moisture (supplied by, for example, addition of water) until the composition gets hard moderately. Kneading can be seen as sufficient when the whole composition becomes wet and the erythritol dissolves partly. Usually, erythritol is mixed well with additives such as a drug, and the mixture is kneaded together with water. In using the kneading machine described in Examples (universal mixing machine), kneading is carried out for about 5 to 15 minutes.

The resulting composition is molded by means of equipment which provides a wet molded solid having shape retention without requiring high pressure, such as a tablet machine. Examples of suitable equipment are a single-shot tablet machine, a molding machine, an extrusion molding machine (e.g., extruder), and the like.

An extruder (preferably a twin-screw extruder) can be used for kneading a mixture of erythritol and a drug or the like, together with moisture fed at a constant rate and, if desired, for molding the blend. In this case, the blend is usually discharged through the die in the form of a strand of a given size, which is cut to length at the outlet of the die to obtain pellets as molded products. If necessary, the pellets can further be molded into another shape by means of a separate molding machine. It is also possible that the extruded blend is supplied to another molding machine where it is molded into a desired shape.

Where an extruder is employed for kneading, the efficiency of kneading is higher than in an ordinary kneading machine (e.g., universal mixing machine) so that the rate of erythritol's dissolving in water is increased, and recrystallization of erythritol in drying under reduced pressure is enhanced. It follows that the resulting solid has increased hardness and takes a longer time for disintegration. Therefore, where kneading is carried out in an extruder, it is preferred to use a mixed solution of water and an organic solvent such as ethanol, preferably an ethanol aqueous solution containing about 25 to 85% by weight of ethanol, for kneading.

Drying under reduced pressure is conducted with an ordinary vacuum drier until the molded product dry thoroughly. It is usually carried out at a degree of vacuum of 10 mmHg or lower, preferably from more than 0 mmHg to 1 mmHg, for 3 hours or more. During the drying step under reduced pressure, the part of the erythritol which has dissolved in water recrystallizes or solidifies, and the erythritol particles are bonded to each other to increase the hardness of the molded product thereby to give a rapidly soluble solid in the oral cavity, such as a tablet, with sufficient hardness. The solid thus obtained has a porous structure or a structure of a porous inside and a dense and hard surface which is formed by the erythritol particles' bonding to each other. If the molded product is dried under atmospheric pressure, removal of water is insufficient, which tends to impair the stability of the drug or the like, or the mutual bonding of erythritol particles on recrystallization or solidification is insufficient for obtaining high hardness.

In the present invention, the term "hard" means that the solid of the present invention has a hardness which can keep the form during the general manufacturing and circulation steps of pharmaceuticals, and preferably has a hardness of about 2 kg or more, more preferably 3 kg or more.

The rapidly soluble solid in the oral cavity according to the present invention is characterized by its hardness enough for withstanding handling during preparation and distribution and capability of rapid disintegration in the presence of water. The rapidly soluble tablet in the oral cavity, for example, can be taken easily without water and disintegrate in the oral cavity in a very short time, needing about 10 seconds for disintegration and melting in the oral cavity. Additionally, because erythritol used as a main component has sweetness with a fresh cool feel, does not cause dental caries, and has no calories, the rapidly soluble solid in the oral cavity can be given to diabetics, the aged and infants without resistance.

The present invention will now be illustrated in greater detail with Reference Examples, Examples, and Test Examples, but it should be understood that the present invention is not construed as being limited thereto. Unless otherwise noted, all the percents are by weight.

REFERENCE EXAMPLE 1

In a kneading machine (universal mixing machine manufactured by San-ei Seisakusho) were put 84 g of erythritol and 10 g of ascorbic acid and kneaded together with 10 g of water. The blend was dried in a hot air drier (60° C.) and granulated through a 16 mesh sieve. The granules were mixed with 5 g of hydroxypropyl cellulose having a low degree of substitution and 1 g of calcium stearate, and the mixture was molded in a tablet machine (HT-AP12SS-II, manufactured by Hata Tekkosho) into rounded tablets each weighing 200 mg and having a diameter of 10 mm.

REFERENCE EXAMPLE 2

In a kneading machine (universal mixing machine manufactured by San-ei Seisakusho) were put 84 g of erythritol and 10 g of ascorbic acid and kneaded together with a solution of 5 g of hydroxypropyl cellulose in 10 g of water. The blend was dried in a hot air drier (60° C.) and granulated through a 16 mesh sieve. The granules were mixed with 1 g of calcium stearate, and the mixture was molded in a tablet machine (HT-AP12SS-II, manufactured by Hata Tekkosho) to obtain rounded tablets each weighing 200 mg and having a diameter of 10 mm.

REFERENCE EXAMPLE 3

Ascorbic acid (1.4 g), 74.1 g of erythritol, and 23.2 g of glucose were ground in a mortar, and the blend was further mixed with 0.9 g of calcium stearate. A 200 mg portion of the resulting powder blend was put in a PTP having a depression of 8 mm in diameter and compressed under a pressure of about 1 kg/pestle, kept at 25° C. and 90% RH for 24 hours, and dried under reduced pressure at 60° C. for 2 hours to obtain tablets.

REFERENCE EXAMPLE 4

Ascorbic acid (21.4 g), 71.4 g of erythritol, and 7.2 g of sucrose were mixed and ground in a mortar. A 210 mg portion of the resulting powder blend was put in a mold having a cavity diameter of 10 mm and compressed under a pressure of about 100 kg/pestle, kept at 30° C. and 89% RH for 18 hours, and dried at 60° C. for 3 hours to obtain tablets.

EXAMPLE 1

Erythritol (90 g) and 10 g of ascorbic acid (vitamin C) were mixed in a kneading machine (universal mixing machine, produced by San-ei Seisakusho), and 2, 5, 10 or 20 ml of water was added thereto, followed by kneading for 10 minutes. The resulting blend was molded in a single-shot tablet machine under a pressure of about 1 kg/pestle, each shot weighing 0.2 g, to obtain tablets having a diameter of 10 mm, which were dried at 40° C. under reduced pressure of 10 mmHg or less for 6 hours to give rapidly soluble tablets in the oral cavity.

TEST EXAMPLE 1

The tablets obtained in Reference Examples 1 to 4 and Example 1 were tested to determine hardness, disintegration time and, dissolving time in the oral cavity. The results obtained are shown in Table 1 below. The hardness was measured with Hardness Tester (Kiya type). The disintegration time was measured six times with a disintegration tester specified in The Pharmacopoeia of Japan (testing liquid: water at 37° C.). The time of dissolving in the oral cavity was the time for a tablet put in the oral cavity of three healthy male adults to completely dissolve or crumble with saliva.

TABLE 1

|  |  | Hardness (kg) | Disintegration Time (sec) | Dissolving Time in Oral Cavity (sec) |
|---|---|---|---|---|
| Reference Ex. 1 |  | 1.1 | 7.2 | 10.0 |
| Reference Ex. 2 |  | 7.6 | >300 | >300 |
| Reference Ex. 3 |  | 6.8 | 120 | 150 |
| Reference Ex. 4 |  | 0.3 | 108 | 95 |
| Ex. 1 | 2 ml | 0.5 | 4.4 | 3.7 |
| (Moisture) | 5 ml | 2.3 | 19.3 | 5.3 |
|  | 10 ml | 3.6 | 14.2 | 7.3 |
|  | 20 ml | 3.5 | 31.8 | 12.3 |

As is apparent from Table 1, the tablets of Reference Example 1, which were prepared by using a disintegrant in a usual manner, have satisfactory disintegration properties but lack sufficient hardness, and the tablets of Reference Example 2, which were prepared by using a water-soluble binder in a usual manner, exhibit high hardness but poor disintegration properties. Besides, the disintegrant used as a vehicle gave a rough feel in the oral cavity. The tablets of Reference Examples 3 and 4, which were prepared by molding a drug, erythritol and glucose or sucrose while moistening in accordance with the teaching of JP-A-9-48726, have insufficient disintegration properties. In particular, the tablets of Reference Example 4, in which drying was carried out under atmospheric pressure, have extremely low hardness. In Example 1, to the contrary, the hardness increases and excellent disintegration behavior are obtained by the addition of 5% or more, based on the solids content, of water. The dissolving time in the oral cavity was as short as about 10 seconds at the most.

EXAMPLE 2

Tablets were prepared in the same manner as in Example 1, except for fixing the amount of water added at 10 ml and varying the amount of ascorbic acid added so as to give an ascorbic acid content of 0, 5, 10, 20, 40 or 60% based on the total weight of erythritol and ascorbic acid.

TEST EXAMPLE 2

The hardness and disintegration time of the tablets prepared in Example 2 were measured in the same manner as in Test Example 1. The results obtained are shown in table 2 below. In Table 2, "Amount Added of VC" means an amount added of ascorbic acid.

TABLE 2

| Amount Added of VC (%) | Hardness (kg) | Disintegration Time (sec) |
|---|---|---|
| 0 | 3.3 | 26.5 |
| 5 | 3.8 | 10.9 |
| 10 | 3.9 | 7.8 |
| 20 | 3.6 | 7.3 |
| 40 | 2.6 | 8.1 |
| 60 | 2.1 | 1.9 |

EXAMPLE 3

Tablets were prepared in the same manner as in Example 1, except for fixing the amount of water added at 10 ml and varying the time of drying under reduced pressure. For comparison, tablets were prepared in the same manner as in Example 1, except for fixing the amount of water added at 10 ml and drying the molded tablets in an ordinary drier at 60° C. for 16 hours.

TEST EXAMPLE 3

The hardness, disintegration time, dissolving time in the oral cavity of the tablets prepared in Example 3 were measured in the same manner as in Test Example 1. The results obtained are shown in Table 3 below.

TABLE 3

| | Hardness (kg) | Disintegration Time (sec) | Dissolving Time in the Oral Cavity (sec) |
|---|---|---|---|
| Ordinary Drying | 0.8 | 132 | 59.3 |
| Time of Drying under Reduced Pressure 1 hr | 2.2 | 9.7 | 11.3 |
| 3 hrs | 2.8 | 8.4 | 13.0 |
| 6 hrs | 2.9 | 7.1 | 11.0 |
| 24 hrs | 2.9 | 7.3 | 15.3 |

The results in Table 3 reveal that ordinary drying under atmospheric pressure does not provide sufficient tablet hardness whereas drying under reduced pressure ensures a hardness of about 3 kg and rapid disintegration when continued for 3 hours or longer. It has now been proved that drying under reduced pressure makes the moisture inside the tablets evaporate rapidly to provide a porous structure while allowing the surface of the tablets to recrystallize to secure sufficient hardness.

EXAMPLE 4

Rapidly soluble tablets in the oral cavity were prepared in the same manner as in Example 1, except for replacing 10 ml of water with 10 ml of a 20% or 50% aqueous solution of ethanol.

TEST EXAMPLE 4

The hardness and disintegration time of the tablets prepared in Example 4 were measured in the same manner as in Test Example 1. The results obtained are shown in Table 4.

TABLE 4

| Ethanol Concentration (%) | Hardness (kg) | Disintegration Time (sec) |
|---|---|---|
| 0 | 3.5 | 10.5 |
| 20 | 2.2 | 6.1 |
| 50 | 1.9 | 5.9 |

It can be seen from Table 4 that use of an ethanol aqueous solution for kneading in place of water results in decreased hardness and accelerated disintegration.

REFERENCE EXAMPLE 5

Tablets were prepared in the same manner as in Example 1, except for replacing erythritol with xylitol or D-mannitol and fixing the amount of water added at 10 ml.

TEST EXAMPLE 5

The hardness and disintegration time of the tablets prepared in Reference Example 5 were measured in the same manner as in Test Example 1. The results obtained are shown in Table 5.

TABLE 5

| | Hardness (kg) | Disintegration Time (sec) |
|---|---|---|
| Xylitol | 2.76 | 59.3 |
| Mannitol | 1.26 | 7.3 |

It can be seen from Table 5 that use of xylitol in place of erythritol results in high hardness but retarded disintegration and that use of D-mannitol in place of erythritol gives tablets which disintegrate more rapid but have very low hardness.

EXAMPLE 5

Tablets were prepared in the same manner as in Example 1, except for fixing the amount of water added at 10 ml and replacing 10 g or 30 g out of 90 g of the erythritol with sucrose or lactose.

TEST EXAMPLE 6

The hardness, disintegration time, and dissolving time in the oral cavity of the tablets prepared in Example 5 were measured in the same manner as in Test Example 1. The results obtained are shown in Table 6 below.

TABLE 6

| | Hardness (kg) | Disintegrating Time (sec) | Dissolving Time in the Oral Cavity (sec) |
|---|---|---|---|
| Sucrose (10 g) | 5.2 | 47.1 | 20 |
| Sucrose (30 g) | 6.8 | 146.3 | 76 |
| Lactose (10 g) | 3.3 | 9.4 | 20 |
| Lactose (30 g) | 4.1 | 14.1 | 13 |

It is seen that addition of sucrose or lactose results in higher hardness than when erythritol is used alone.

However, the disintegration time becomes longer as the amount of sucrose increases.

EXAMPLE 6

Tablets were prepared in the same manner as in Example 1, except for fixing the amount of water added at 10 ml and replacing ascorbic acid with 10 g of ipidacrine hydrochloride hydrate (treating agent for Alzheimer's disease).

EXAMPLE 7

Ten grams of Acetaminophen and 90 g of erythritol were mixed and fed to an extruder (KEX-25, manufactured by Kurimoto Tekko, Ltd.) at a rate of 50 g/min, kneaded together with water fed at a rate of 4 g/min, extruded through a die of 4 mm in diameter, and cut to about 5 mm length. The resulting pellets were dried in a vacuum drier for 6 hours to obtain a rapidly soluble preparation in the oral cavity.

EXAMPLE 8

(a) A mixture of 270 g of erythritol and 30 g of citric acid was fed to an extruder (REX-25, manufactured by Kurimoto Tekko, Ltd.) at a rate of 40 g/min, kneaded together with water fed at a rate of 4 g/min at 150 rpm, extruded through a die of 15 mm in diameter, and cut to 10 mm length. The resulting extruded cylinders were dried in a vacuum drier for 16 hours to obtain rapidly soluble tablets in the oral cavity.

(b) Rapidly soluble tablets in the oral cavity were prepared in the same manner as in (a), except for feeding a 25%, 50% or 75% aqueous solution of ethanol at a rate of 4 g/min in place of water.

TEST EXAMPLE 7

The tablets obtained in Example 8 were tested to determine hardness and disintegration time. The hardness as measured with a texture analyzer (manufactured by Stable Micro Systems). The disintegration time was measured in the same manner as in Test Example 1. The results obtained are shown in Table 7 below.

TABLE 7

| Ethanol Concentration (%) | Hardness (kg) | Disintegration Time (sec) |
| --- | --- | --- |
| 0 | 21.3 | 63.3 |
| 25 | 19.0 | 18.0 |
| 50 | 17.0 | 13.7 |
| 75 | 15.4 | 11.5 |

As can be seen from Table 7, where the mixture is kneaded in an extruder using water as a medium, the resulting tablets have a long disintegration time, while use of an aqueous ethanol solution in place of water provides tablets showing more rapid disintegration.

EXAMPLE 9

Tablets were obtained in the same manner as in Example 7, except for replacing Acetaminophen with 10 g of α-tocopherol.

EXAMPLE 10

A hundred grams of erythritol was put in a kneading machine (universal mixing machine manufactured by San-ei Seisakusho) and kneaded together with 10 g of water. The resulting blend was compressed into tablets each weighing 0.2 g by means of a mold having a cavity diameter of 10 mm and a pestle under a pressure of about 1 kg/pestle. The molded tablets were dried under reduced pressure (10 mmHg or less) at 40° C. for 6 hours to obtain a rapidly soluble solid in the oral cavity sweetener.

EXAMPLE 11

A rapidly soluble solid in the oral cavity sweetener was prepared in the same manner as in Example 10, except for replacing 100 g of erythritol with a mixture consisting of 99 g of erythritol, 0.5 g of aspartame, and 0.5 g of Stevia invert sugar.

EXAMPLE 12

Rapidly soluble tablet candies were prepared in the same manner as in Example 10, except for replacing 100 g of erythritol with a mixture consisting of 85 g of erythritol, 10 g of maltitol, 5 g of vitamin C, and a small amount of a lemon flavor.

While the invention has been described in detail and with reference to specific examples thereof, it will be apparent to one skilled in the art that various changes and modifications can be made therein without departing from the spirit and scope thereof.

This application is based on Japanese application No. Hei 9-329743, the entire contents of which are incorporated hereinto by reference.

What is claimed is:

1. A process for producing a solid which is rapidly soluble in the oral cavity, wherein the solid has a porous structure, which process comprises the steps of:

preparing a composition consisting essentially of 80 to 99.9% by weight of erythritol, a component selected from the group consisting of a drug, a pharmaceutically acceptable additive, a food, and a food additive, and moisture in an amount of 5 to 20% by weight based on the solid content of the composition, wherein said pharmaceutically acceptable additive is selected from the group consisting of sucrose, lactose, xylitol, D-mannitol, maltitol, lactitol, magnesium stearate, calcium stearate, talc, light silicic acid anhydride, silicon dioxide hydrate and a surfactant, kneading the composition, molding the composition, and drying the molded composition under reduced pressure.

2. The process according to claim 1, wherein the moisture is water or a mixed solution of water and an alcoholic organic solvent.

3. The process according to claim 1, wherein the drying under reduced pressure is carried out at a degree of vacuum of 10 mmHg or lower for 3 hours or more.

4. The process according to claim 1, wherein the kneading is carried out using an extruder.

5. The process according to claim 4, wherein the moisture is an ethanol solution.

6. The process according to claim 5, wherein the ethanol solution has an ethanol concentration of 25 to 85% by weight.

7. The process according to claim 1, wherein the solid, upon administration to the oral cavity, dissolves in or crumbles with saliva in about 20 seconds or less and disintegrates in 30 seconds or less.

8. The process according to claim 7, wherein the solid, upon administration to the oral cavity, dissolves in or crumbles with saliva in about 10 seconds or less and disintegrates in 10 seconds or less.

9. The process according to claim 1, wherein the solid has a dense and hard surface.

10. The process according to claim 1, wherein the solid has a surface hardness of 3 kg or more.

11. The process according to claim 9, wherein the dense and hard surface of the solid is formed by erythritol particles' bonding to each other.

12. The process according to claim 1, wherein the component is a drug.

13. The process according to claim 12, wherein the solid is a tablet.

14. The process according to claim 1, wherein the solid is a food product.

15. The process according to claim 14, wherein the food product is a sweetner or a tablet candy.

16. The process according to claim 1, wherein said drug is selected from the group consisting of a drug for the treatment of senile dementia, an antipyretic, an analgesic, an anti-inflammatory agent, an antitussive, a vitamin, a psychotrophic agent, an antivertigo agent, a hypnotic sedative, a gastrointestinal drug, an antiarrhythmic and a hypotensive agent.

17. The process according to claim 1, wherein said food or food additive is selected from the group consisting of a high sweetness sweetener, saccharin sodium, Acesulfame K, a sugar alcohol, a saccharide, a flavorant, a coloring agent, a vitamin, an acidulant, a fruit juice, cacao powder, coffee powder and calcium powder.

18. The process according to claim 17, wherein said high sweetness sweetener is selected from the group consisting of stevioside, rebaudioside and enzyme-treated stevia.

19. The process according to claim 17, wherein said sugar alcohol is selected from the group consisting of sorbitol, maltitol, xylitol, lactitol, isomalt, and a reducing starch saccarification product.

20. The process according to claim 17, wherein said saccharide is selected from the group consisting of sucrose, glucose, maltose, isomerized sugar, fructo-oligosaccharide and isomalto-oligosacchariade.

21. The process according to claim 17, wherein said flavorant is selected from the group consisting of lemon flavor, orange flavor, cinnamon flavor, rosemary flavor and menthol flavor.

22. The process according to claim 17, wherein said colorant is selected from the group consisting of food yellow No. 5 and food red No. 2.

23. The process according to claim 17, wherein said vitamin is selected from the group consisting of vitamin A, vitamin $B_1$, vitamin $B_2$, vitamin $B_6$, vitamin $B_{12}$, vitamin C and vitamin E.

24. The process according to claim 17, wherein said acidulant is selected from the group consisting of malic acid, citric acid and tartaric acid.

25. The process according to claim 17, wherein said fruit juice is selected from the group consisting of grape juice and citrus juice.

* * * * *